(12) United States Patent
Demou et al.

(10) Patent No.: US 10,368,757 B2
(45) Date of Patent: Aug. 6, 2019

(54) METHODS AND SYSTEMS FOR ADVERSE EVENT PREDICTION USING PUMP OPERATING DATA

(71) Applicant: HeartWare, Inc., Miami Lakes, FL (US)

(72) Inventors: Zoe Demou, Miami, FL (US); Antonio Luiz Silva Ferreira, Davie, FL (US)

(73) Assignee: HeartWare, Inc., Miami Lakes, FL (US)

( * ) Notice: Subject to any disclaimer, the term of this patent is extended or adjusted under 35 U.S.C. 154(b) by 120 days.

(21) Appl. No.: 15/340,174

(22) Filed: Nov. 1, 2016

(65) Prior Publication Data

US 2017/0119256 A1    May 4, 2017

Related U.S. Application Data

(60) Provisional application No. 62/249,601, filed on Nov. 2, 2015.

(51) Int. Cl.
| | |
|---|---|
| *A61M 1/12* | (2006.01) |
| *A61B 5/029* | (2006.01) |
| *A61B 5/11* | (2006.01) |
| *A61B 5/145* | (2006.01) |
| *A61B 5/00* | (2006.01) |
| *A61M 1/10* | (2006.01) |

(52) U.S. Cl.
CPC ............ *A61B 5/029* (2013.01); *A61B 5/1118* (2013.01); *A61B 5/14535* (2013.01); *A61B 5/4845* (2013.01); *A61B 5/686* (2013.01); *A61B 5/7235* (2013.01); *A61M 1/1086* (2013.01); *A61M 1/122* (2014.02); *A61M 2205/702* (2013.01)

(58) Field of Classification Search
CPC ....... A61M 1/1086; A61B 5/024; A61B 5/026
See application file for complete search history.

(56) References Cited

U.S. PATENT DOCUMENTS

| | | | |
|---|---|---|---|
| 8,512,013 B2 | 8/2013 | LaRose et al. | |
| 2012/0245681 A1 | 9/2012 | Casas et al. | |
| 2013/0006130 A1* | 1/2013 | Olde ..................... | A61B 5/026 |
| | | | 600/504 |
| 2015/0367048 A1 | 12/2015 | Brown et al. | |

FOREIGN PATENT DOCUMENTS

WO    2014197558 A2    12/2014

OTHER PUBLICATIONS

International Search Report and Written Opinion dated Mar. 23, 2017, for corresponding International Application No. PCT/US2016/059832; International Filing Date: Nov. 1, 2016 consisting of 17 pages.

* cited by examiner

*Primary Examiner* — Allen Porter
(74) *Attorney, Agent, or Firm* — Christopher & Weisberg, P.A.

(57) ABSTRACT

The present disclosure provides for each of a method of characterizing divergence of a monitored flow rate of blood through an implantable blood pump, and a method of predicting an upcoming adverse cardiac event using operating data of the blood pump, such as the characterized divergence data. Predicting an upcoming adverse cardiac event may be further based on similar operating data from a plurality of other implantable blood pumps.

8 Claims, 8 Drawing Sheets

METHODS AND SYSTEMS FOR ADVERSE EVENT PREDICTION USING PUMP OPERATING DATA

CROSS-REFERENCE TO RELATED APPLICATIONS

This application claims the benefit of the filing date of U.S. Provisional Patent Application No. 62/249,601 filed Nov. 2, 2015, the disclosure of which is hereby incorporated herein by reference.

BACKGROUND

Implantable blood pumps may be used to provide cardiac support to patients with late stage heart disease. Blood pumps operate by receiving blood from a patient's heart or the vascular system and impelling the blood into the patient's arterial system. By adding momentum and pressure to the patient's blood flow, blood pumps may augment or replace the pumping action of the heart.

For example, a blood pump may be configured as ventricular assist device or "VAD", when it is used to assist the pumping action of the left or right ventricle. The device typically draws blood either from the left ventricle of the heart and discharges the blood into the aorta or from the right ventricle and discharges into the pulmonary artery. Some blood pumps may provide partial support for the patient's heart, in which case the pump may draw blood from the patient's atria. Additionally, in a case of partial support, the pump may discharge into the patient's subclavian artery.

Blood pumps provide clinically useful assistance to the heart by impelling blood at a substantial blood flow rate through the vasculature. For an adult human patient, a ventricular assist device may be arranged to pump blood at about 1-10 liters per minute at a differential pressure across the pump of about 10-110 mm Hg, depending on the site of implantation and the needs of the patient. The needs of the patient may vary with age, height, and other factors.

Some aspects of the present invention provide for: (a) regularly monitoring the patient to ensure that the patient is not at risk of certain cardiovascular health conditions, such as a transient ischemic attack (TIA) or cerebrovascular accident (CVA), e.g., ischemic stroke, hemorrhagic stroke; and (b) assisting clinicians in their decisions about patient treatment. Methods for monitoring the patient generally require measurements, such as a patient's vitals, to be taken by a clinician and, therefore, those measurements are inconvenient for regular monitoring, let alone for continuous monitoring. Therefore, it is desirable to implement in routine clinical monitoring a system that is not only capable of monitoring operation of the blood pump which it controls, but is further capable of monitoring a patient's health based on the information gathered from the pump. The patient's health monitoring may be performed locally (in the pump controller itself) or remotely, in which case data gathered from the pump is sent to a computer center, following the remote patient monitoring paradigm.

It is further desirable to provide a clinical decision system that can predict an oncoming occurrence of an adverse cardiovascular or cerebrovascular health condition based on the information gathered from the pump.

SUMMARY

One aspect of the present disclosure provides for a method of characterizing divergence of a monitored flow rate of blood through an implantable blood pump. The method may include repeatedly performing over time: (i) determining a flow rate of blood through the pump at a then-current time, (ii) calculating an average flow rate of blood through the pump over a first period of time preceding the then-current time, (iii) calculating a divergence value, which is representative of a difference between the average flow rate and the determined then-current flow rate, wherein the divergence of flow rate is characterized based on a sum of the calculated divergence values. A sum of calculated divergence values may be repeatedly calculated, such that for a given then-current time, the summed divergence values are the divergence values calculated over a second period of time immediately preceding the then-current time. In some examples, the second period of time may be shorter than the first period of time. For instance, the second period of time may be about three hours, whereas the first period of time may be about three days. In some examples, the calculated average flow rate may be a moving average, whereby the first period of time immediately precedes the then-current time.

The present disclosure also provides for a method of predicting an adverse event based on flow rate data from an implantable blood pump. The method may include a method of characterizing divergence of a monitored flow rate as described herein, whereby the sum of calculated divergence values is repeatedly calculated, and each of the summed divergence values is associated with its corresponding then-current time. The method may further include compiling the summed divergence values into a waveform (e.g., a time-domain waveform), and predicting an adverse event based on one or more features of the waveform. Alternatively or additionally, the method may further include comprising sorting the summed divergence values by magnitude, and predicting an adverse event based on the highest magnitude summed divergence values.

The present disclosure also provides for a method of predicting an upcoming adverse event for a user of a first implantable blood pump based on information derived from first operating data of the first implantable blood pump, and further based on information derived from segments of second operating data of the first implantable blood pump and/or one or more other implantable blood pumps for which it is known whether each segment corresponds to occurrence or non-occurrence of an adverse event. For each implantable blood pump, the operating data may be gathered over a duration of time, and the information may be derived from a waveform constructed based on the operating data. The method may include: (i) acquiring the first operating data from the first implantable blood pump, (ii) deriving information from a waveform constructed based on the operating data, (iii) accessing information derived from a waveform constructed based on the segments of second operating data (from the first or other implantable pumps) for which at least a first portion of the information corresponds to non-occurrence of an adverse event and at least a second portion of the information corresponds to occurrence of an adverse event, (iv) for at least two waveform features of the derived information, comparing said information derived from the first operating data to said information derived from the second operating data, and (v) based on the comparison, determining whether the first operating data correlates with the first or second portions of the second operating data, whereby a correlation to the second portion of the second operating data is a prediction of an upcoming adverse event within the predetermined time span.

In some examples, the operating data for each implantable blood pump may be a waveform of a flow rate of blood in the implantable blood pump. Also, in some examples, the predetermined time span may be between about one and about seven days, or between about one day and about one month, or between about six days and sixty days. For each blood pump for which segments of second operating data are accessed, the segments of second operating data of that blood pump may correspond to at least about one month of operating data. In some cases, those segments of second operating data may be accessed at least in part from the first implantable blood pump. Those segments of second operating data accessed from the first implantable blood pump may be logged at least about one year prior to being accessed. Additionally or alternatively, the second operating data may include more than two portions, whereby at least one portion of the second operating data corresponds to a particular type of adverse event.

At least one of the waveform features may be: an integral between two consecutive zero-crossing nodes, an integral between two non-consecutive zero-crossing nodes; a maximum calculated divergence of flow; a minimum calculated divergence of flow; a number of positive peaks over a time segment between two consecutive zero-crossing nodes; a number of positive peaks over a time segment between two consecutive zero-crossing nodes; a frequency of positive peaks between two consecutive zero-crossing nodes; a frequency of negative peaks between two consecutive zero-crossing nodes; a slope between a zero-crossing nodes and a positive peak; or a slope between a zero-crossing nodes and a negative peak, and a slope between local extrema. At least two of the waveform features may be selected from the above group.

Comparison of the waveform features may be performed using a data mining analysis, such as a linear discriminant analysis, a cluster analysis, or a Bayesian analysis, or using a neural network. Alternatively or additionally, the waveform features may be selected such that the first and second pluralities of other blood pumps are separated into non-overlapping classes.

In the event of a prediction of an upcoming adverse event within the predetermined time span, the method may further include outputting a notification of the prediction and a percentage likelihood of the predicted event occurring. An analytical basis for the prediction may also be outputted. The analytical basis for the prediction may include an indication of whether second operating data that correlates with the first operating data was accessed from the first implantable blood pump or from one or more of the other implantable blood pumps. The prediction may have any one or more of: a balanced accuracy of at least about 86%; a sensitivity of at least about 78%; a specificity of about 99%; or an area-under-curve accuracy of about 99%.

The method may further include accessing data relating to a physiological factor of a user of said first blood pump (e.g., activity level, hematocrit level, medication of the user, pathology of a condition of the user, a previously recorded adverse event of the user, etc.). The determination of whether the information derived from the first operating data of said first blood pump correlates with the information derived from the first or second portions of information derived from the second operating data may be based further on the physiological factor data.

Yet a further aspect of the present disclosure provides for a method of detecting thrombosis in an implantable blood pump. The method may include: (i) repeatedly estimating a flow rate of blood through the pump over time, (ii) repeatedly calculating a moving flow rate average of the estimated flow rate, (iii) repeatedly calculating a divergence between a then-current estimated flow rate and the then-current moving flow rate average, (iv) repeatedly calculating a moving sum of the calculated divergence, and (v) determining the presence of thrombosis in the blood pump based on the calculated moving sum. Optionally, the method may further include: (vi) receiving a first data set of moving sum data during which thrombosis did not occur, (vii) receiving a second data set of moving sum data during which a thrombosis did occur, and (viii) comparing the calculated moving sum to each of the first and second data sets, wherein determining the presence of thrombosis in the blood pump based on the calculated moving sum is based on said comparison.

Yet a further aspect of the present disclosure provides for a VAD controller which can be used to regularly monitor the patient to ensure that the patient is not at risk of certain heart-related health conditions, such as a transient ischemic attack (TIA) or cerebrovascular accident (CVA).

DETAILED DESCRIPTION

The present disclosure provides methods, systems and devices and methods that are capable of collecting and characterizing data that may be used to predict an oncoming occurrence of a heart-related health condition or other adverse event based on collected information, and may be further capable of notifying the patient or clinician in the event of such an oncoming occurrence. Adverse events may include any of bleeding, infection, cardiovascular health condition, cerebrovascular adverse event, hematocrit changes, VAD peripheral malfunction etc.

One example blood pump system for which the present disclosure may be applied is the HVAD® Pump manufactured by HeartWare Inc. in Miami Lakes, Fla., USA. The HVAD® Pump is a centrifugal pump, and is further discussed in U.S. Pat. No. 8,512,013, the disclosure of which is hereby incorporated herein in its entirety. In operation, the blood pump draws blood from a source such as the right ventricle, left ventricle, right atrium, or left atrium of a patient's heart and propels the blood into an artery such as the patient's ascending aorta or peripheral artery. Due to the nature of the application, the pumping mechanism must be highly reliable. Patient comfort is also a significant consideration. In addition to the pumping mechanism, the device may include a controller and the drive electronics for the pumping mechanism. The controller and drive electronics may receive power from an external power source. That power may be used to drive a motor of the pumping mechanism at a desired speed.

Another example blood pump system to which the present disclosure may be applied is the MVAD® Pump, also manufactured by HeartWare Inc. The MVAD® Pump is an axial pump, and is further discussed in U.S. Publication No. 2012/0245681, the disclosure of which is hereby incorporated herein in its entirety. In operation, the pump similarly draws blood toward the patient's ascending aorta or peripheral artery, but in the same direction from which the blood was drawn from the ventricle or atrium of a patient's heart. Each of the HVAD and MVAD systems includes control circuitry for monitoring operation data of the respective pumps, as well as for controlling operation of the pumps.

Figure 1:
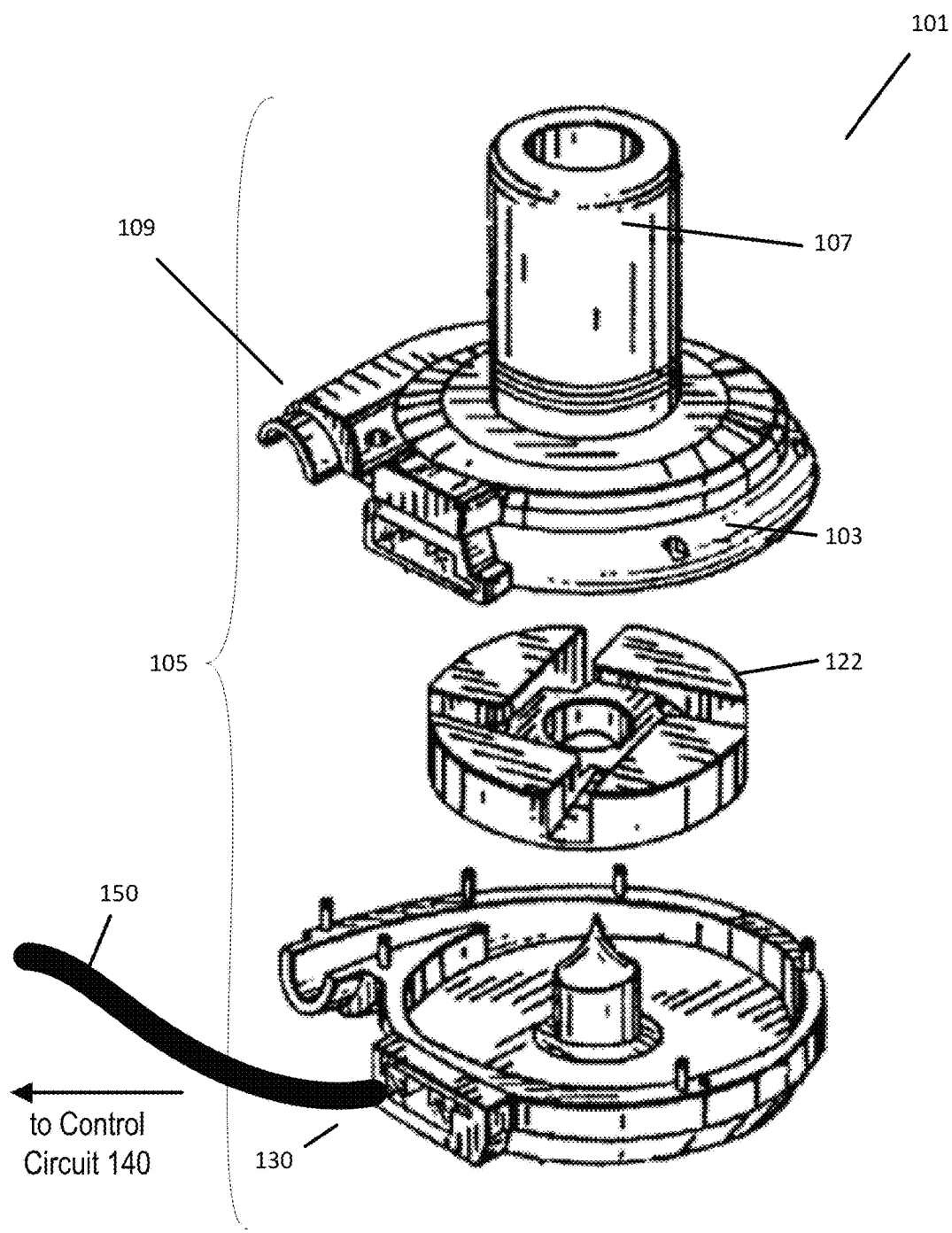
FIG. 1 is an exploded perspective view of a blood pump in accordance with an embodiment of the disclosure.

FIG. 1 depicts an HVAD pump by way of example. As depicted in FIG. 1, the pump 101 includes a housing 105 including interlocking casings to form a closed pumping chamber 103 between them. Blood is supplied to the pump 101 through an axial inlet cannula 107 adapted for apical insertion into a heart ventricle. The cannula 107 is affixed to or may be integral with the housing 105 and is in fluid flow communication with the pumping chamber 103. Blood exits the pumping chamber 103 through an outlet in a direction substantially perpendicular to the longitudinal axis of the inlet cannula 107. The outlet of the housing can be connected to an artery of the patient, such as the aorta, by an outlet cannula 109.

A rotor or pump impeller 122 is located within the pumping chamber 103. The rotor incorporates one or more permanent magnets (not shown), and sets of electrical coils (not shown) are disposed in fixed locations within housing 105. The coils and magnets form a motor. In operation, blood entering the cannula 107 from a heart ventricle passes into the pumping chamber 103 where it is engaged by the rotating impeller 122. Blood entering the pumping chamber from the cannula 107 is redirected from axial flow exiting the cannula to a radial flow within which the impeller 122 is submerged.

A power and control cable 150 extends through a feedthrough 130 on the housing, and connects the coils within the housing to a control circuit 140. Control circuit 140 is connected to a source of electrical energy (not shown), which may include a storage battery, a mains power connection or both. As further discussed below, control circuit 140 is arranged to energize the coils of the pump in sequence so as to apply a rotating magnetic field within the housing and drive rotor 122 in rotation so that, in operation, the pump draws blood from the left ventricle V of the patient's heart and propels the blood through outflow cannula 109 into the patient's aorta.

The control circuit 140 monitors and further controls operation of the pump 101. The control circuit functions may be implemented at least in part by a general-purpose processor, as shown in the example implementation of FIG. 2. As shown, the control circuit 140 is implemented using a processor 210, a memory 220, data 230, instructions 240, and a pump interface 250. Interface 250 may include components such as power semiconductors connected to the coils of the pump, as well as one or more sensors for detecting voltages on the pump coils. The control circuit 140 may optionally include an I/O interface 252 which connects the control circuit 140 to one or more I/O devices 260 adapted to input information into the control circuit, output information from the control circuit, or both. The interface 250 may be an analog interface or a digital interface.

Memory 220 stores information accessible by processor 210, including instructions 240 that may be executed by the processor 210. The memory also includes data 230 that may be retrieved, manipulated or stored by the processor 210. The memory may be of any type capable of storing information accessible by the processor, such as a hard-drive, memory card, ROM, RAM, DVD, CD-ROM, write-capable, and read-only memories. The processor 210 may be any well-known processor, such as commercially available processors. Alternatively, the processor may be a dedicated controller such as an ASIC.

Data 230 may be retrieved, stored or modified by processor 210 in accordance with the instructions 240. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

The data 230 may include operation data of the blood pump, such as power data (e.g., current supplied to the pump) 236, pump rotational speed data 234, pressure differential between an inlet and outlet of the pump, and flow rate of blood through the pump 232. Such data may be sampled and analyzed from the electrical signals of the control circuit of the blood pump.

Figure 3:
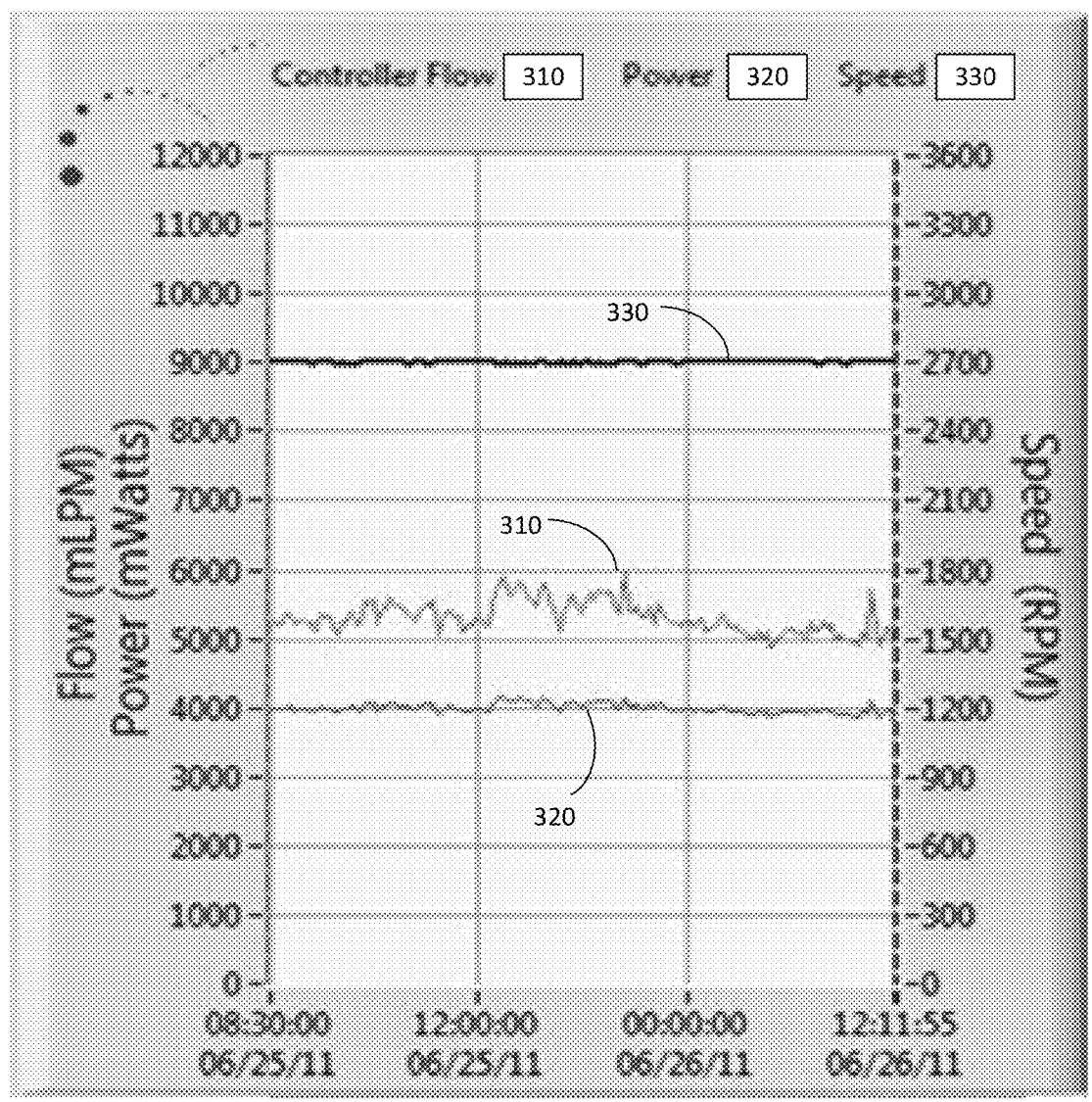
FIG. 3 is a visual representation of time-ordered operation data collected from a blood pump in accordance with an embodiment of the disclosure.

FIG. 3 depicts an example of raw log data that may be collected by the blood pump control circuit in order to monitor the VAD. The raw data includes several operating parameters of the monitored VAD, including flow rate of blood exiting the pump 310, motor speed of the pump motor 320, and power supplied from the pump drive circuit to the pump motor 330. The data is referred to as "raw" in that it has not yet been analyzed, characterized or otherwise processed in accordance with the methods described herein.

The instructions 240 stored in the memory may include one or more instruction sets or modules for performing certain operations. One such module may be a flow estimation module 242 for performing the steps required to estimate a flow rate of blood through the pump. The flow estimation module may be configured to estimate a flow rate of blood through the pump using a model. Models for a centrifugal pump may determine blood flow rate based in part on the acceleration of the rotor of the pump, an amount of electrical current supplied to the pump, and possibly the viscosity of the patient's blood (e.g., based on hematocrit levels). Models for an axial flow pump may determine blood flow rate based further in part on a back electromotive force induced by the impeller on the coils of the rotor.

In other example systems, other parameters indicative of flow may be used, and/or different calculations may be employed, to estimate a flow rate of blood. Alternatively, flow rate data may be gathered using direct measurements, such as with an ultrasonic flow meter.

The control circuit may be further operable to log the estimated, or measured, flow rate data. In some examples, the control circuit may perform additional computations based on the logged data. Some examples of such computations (e.g., maximum, minimum, average, or amplitude) are provided in commonly owned U.S. Patent Publication No. 2015/0367048, the disclosure of which is incorporated herein in its entirety.

Another such module may be a pump control module 244 for controlling the speed of the pump speed control module. In some examples, rotational speed of the pump may be controlled based on the logged data, such as if an estimated flow rate (or function of the estimated flow rate) were to meet or exceed a threshold value.

Figure 2:
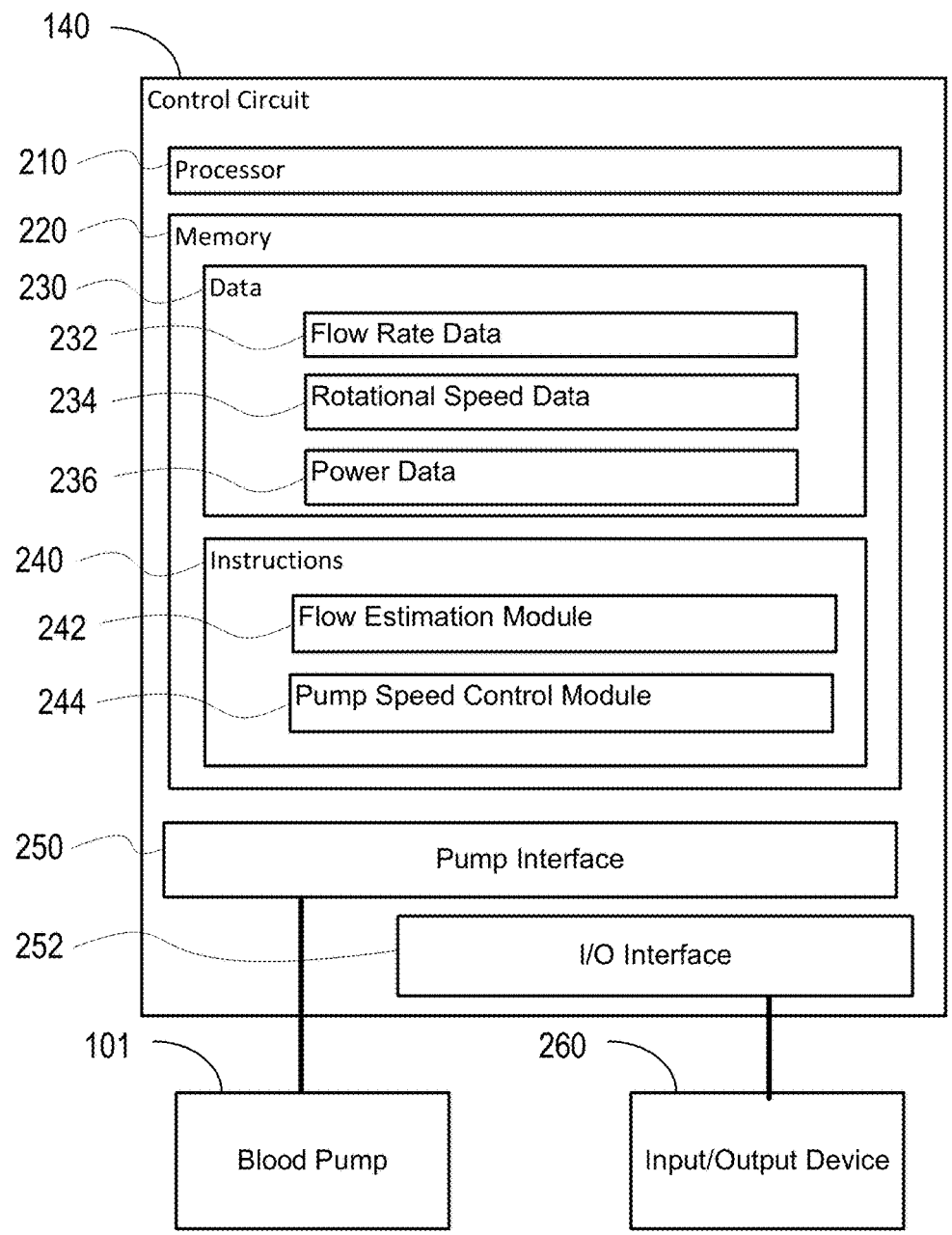
FIG. 2 is a block diagram of a control circuit in accordance with an embodiment of the disclosure.

Although FIG. 2 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

In some examples, the control circuit may not be capable of performing all or some of the methods described herein (e.g., due to memory constraints, processing constraints, lack of network connectivity, etc.). In such cases, the control circuit may output the collected and logged data to a different processor for further analysis. Thus, the methods described below may be performed by an external processor that receives the logged data from the VAD control circuit. Alternatively, those skilled in the art would recognize that the processor of a VAD control circuit that is capable of performing the methods described herein may be assigned to perform such methods, in which case the logged data may be analyzed in the manner described herein without even having to output the data.

Figure 4:
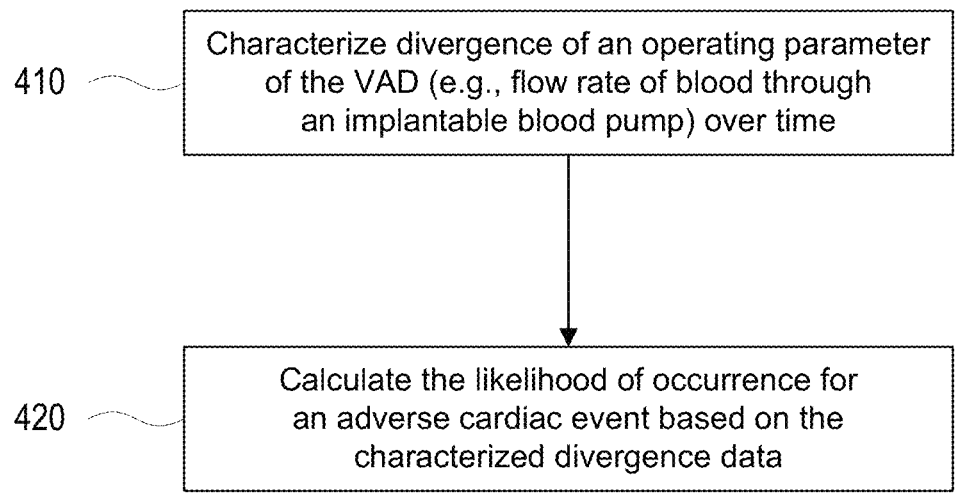
FIG. 4 is a flow chart of an example method in accordance with an embodiment of the disclosure.

FIG. 4 provides an example method 400 for predicting an oncoming occurrence of a heart-related health condition based on the information gathered from the VAD. At 410, divergence of an operating parameter of the VAD (e.g., flow rate of blood through an implantable blood pump) is characterized over time. The characterized divergence data is indicative of changes in the operating parameter over time for the specific VAD under analysis. For many operating parameters, such as the flow rate of blood exiting the pump, it is common for the operating parameter to be constantly fluctuating. In such cases, instead of monitoring the constant fluctuations of the operating parameter, the parameter may be characterized to indicate when there has been a sustained change over an extended period of time, such as a sustained increase or decrease to average flow.

At 420, the likelihood of occurrence for an adverse cardiac event is calculated based on the divergence data characterized at 410. Upcoming adverse cardiac events often cannot be identified using individual and isolated features of the collected data. Rather, the data is analyzed based on trends, combinations of features, etc. In this regard, often the more data available to analyze the divergence data, the better the resulting calculation may be. In this regard, the likelihood of occurrence for an adverse cardiac event may be calculated based further on information derived from divergence data gathered from other VADs as well.

Figure 5:
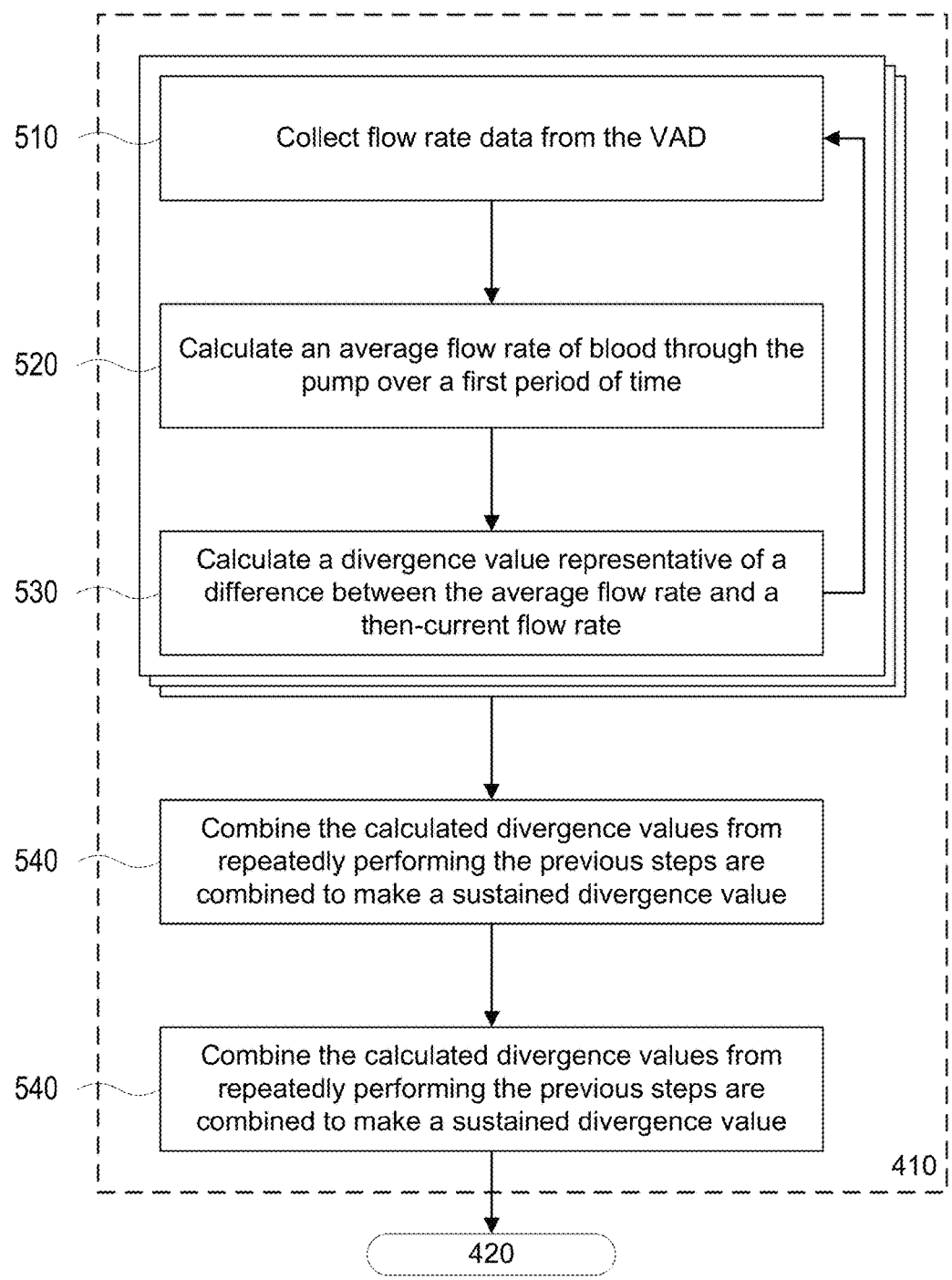
FIG. 5 is an example flow chart expanding on a first step of the method of FIG. 4.
Figure 6:
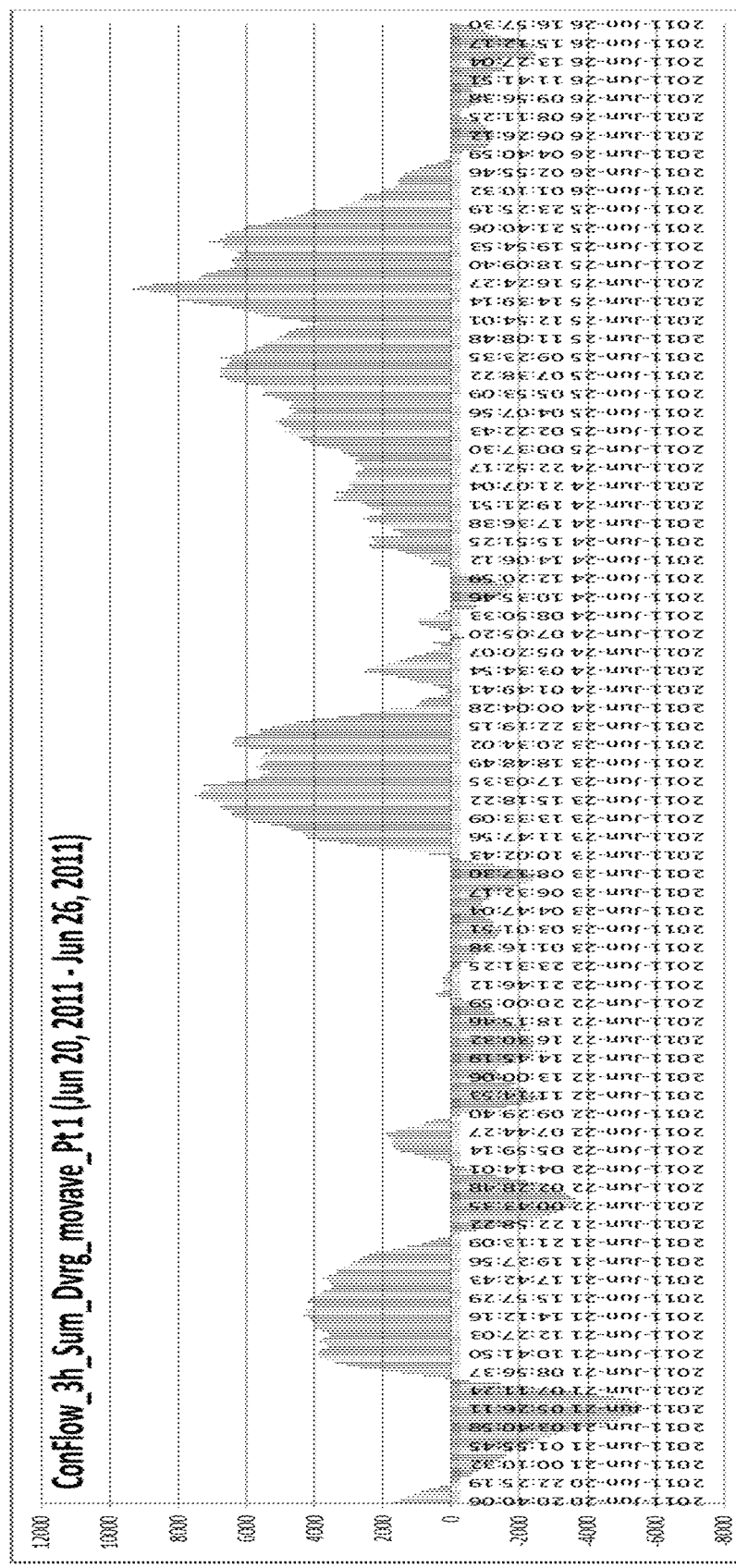
FIG. 6 is a visual representation of time-ordered divergence data in accordance with an embodiment of the disclosure.

The method 400 of FIG. 4 may itself be divided into smaller steps. FIG. 5 provides an example method 500 for performing 410, the characterization of divergence of a VAD parameter, where the parameter selected is flow rate data, although other parameters may be selected instead. FIG. 6 provides an example method 600 for performing 420, the determining of a likelihood of an adverse cardiac event, based on the outcome of the method of FIG. 5.

Turning first to FIG. 5, at 510, flow rate data is collected from the VAD, either by estimation, derivation, or direct measurement. The flow rate data may be collected by a flow estimation module, such as the one described in connection with FIG. 2.

At 520, an average flow rate of blood through the pump over a first period of time (e.g., about seventy-two hours) is calculated. The average flow rate may be a moving average, repeatedly calculated over time. In other words, the first period of time may be a fixed duration, such as seventy-two hours, and all data points collected within the previous duration immediately preceding the then-current time (e.g., the last seventy-two hours) are averaged.

At 530, a divergence value is calculated. The divergence value may be representative of a difference between the average flow rate (as described above) and a then-current flow rate. In this regard, the divergence value itself is indicative of how different the flow rate at a given moment is from the average flow rate over a longer course of time. In some examples, the divergence value may be the difference between average flow rate and actual, then-current flow rate itself. In other examples, the divergence value may be a square of such difference, or other modified value (e.g., difference to the ⅓ power, etc.)

Since the flow rate of blood through a VAD of even a healthy patient is not a constant value, and may vary depending on the patient's activity level, medication regimen, hematocrit, or other factors, a single divergence value is not by itself indicative of a sustained divergence from normal operating parameters of the VAD. Therefore, in order to characterize divergence of the operating parameter, it is necessary to detect a sustained divergence from normal operation of the VAD. In this regard, 510-530 of method 500 are repeatedly performed, thereby repeatedly collecting divergence values over a period of time.

Along with the repeated performance of 510-530, at 540, the calculated divergence values are combined to make a sustained divergence value. For example, the divergence values may be averaged to show an overall divergence over a period of time. Alternatively, a sum of the divergence values (without dividing by the number of values) may be used so as to amplify or accentuate the amount of sustained divergence over time. A sustained divergence value may be calculated from the divergence values over a second period of time, generally shorter than the first period of time (e.g., about three hours). The second period is shorter than the first period since it is intended to show a relative short-term divergence from a relative long-term normal mode of operation.

In some examples of FIG. 5, calculating a summed or combined divergence value may be performed repeatedly, such that, for every calculation of a divergence value at 510-530, a new summed divergence value may be calculated. In other examples, a new summed divergence value may be calculated with less frequency than the divergence values (e.g., one new summed divergence value for every two divergence values). In this regard, 510-530 may optionally be repeated without performing 540. In some examples, performance of 540 may be performed in parallel with 510-530 at predefined time intervals, based on an amount of data collected since a previous iteration, or based on manual input.

In either of the above cases, the divergence of estimated flow rate may then be characterized based on the sum of the calculated divergence values. In the example of FIG. 5, at 550, the summed divergence values are compiled, thereby effectively building a waveform of summed divergence values over time. The summed divergence values may be compiled in a time-domain, so as to create a waveform of summed divergence values. An example time-domain waveform of summed divergence data is shown in FIG. 6.

Using a sum of divergence values, as compared to merely a waveform of operating data, or a waveform of divergence values, provides for a smoother and enhanced waveform for further evaluations. Thus, the divergence and summing operations of the previous steps essentially function as a filter for the operation data derived from the VAD.

Those skilled in the art would understand that the data need not necessarily be visualized as a waveform in order to perform the further computations described herein (e.g., slope, maxima), but rather is shown as a waveform for purposes of illustrative clarity. Ultimately, the same or similar computations may be performed mathematically on time-ordered data without graphical visualization of the data.

Figure 7:
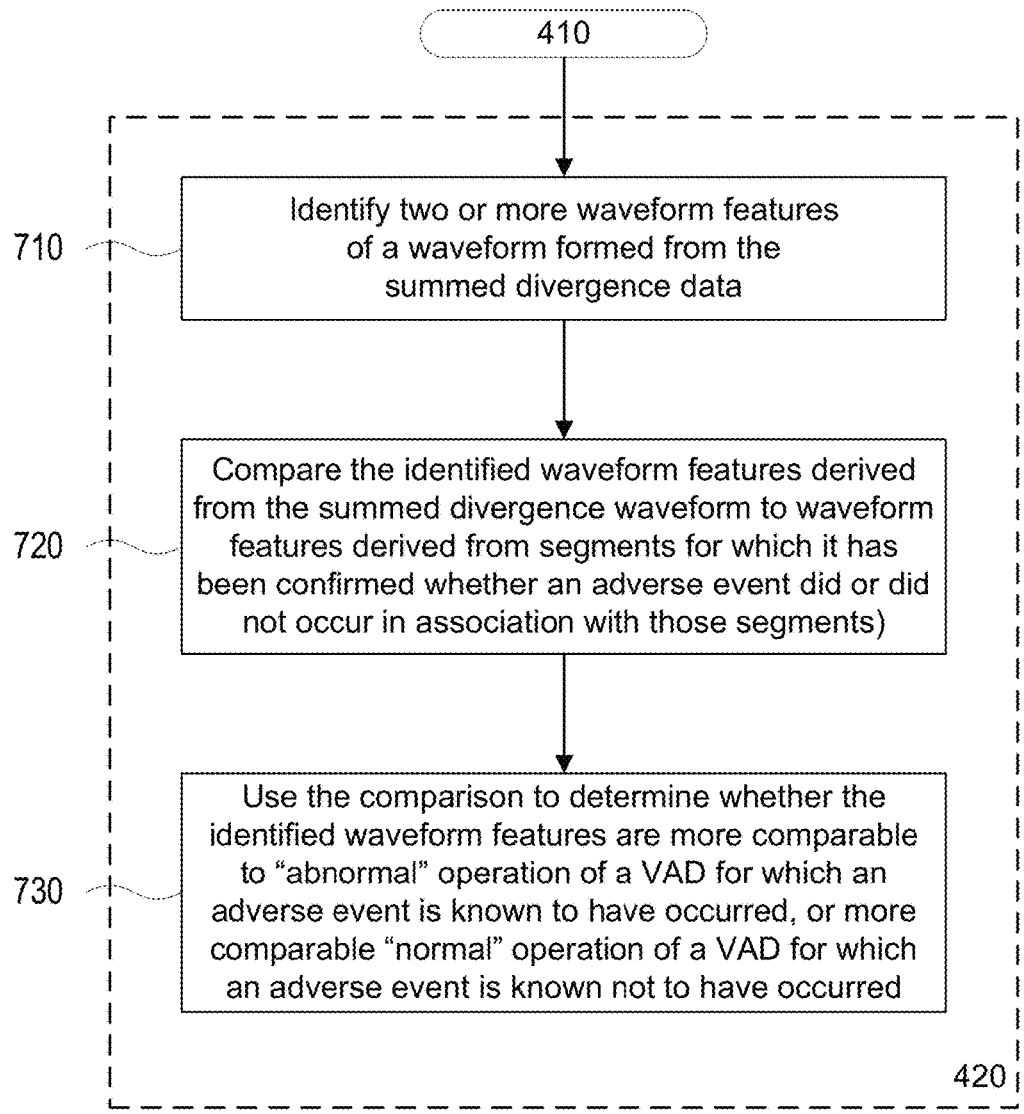
FIG. 7 is an example flow chart expanding on a second step of the method of FIG. 4.

FIG. 7 provides an example method 700 for predicting the likelihood of occurrence for an adverse cardiac event. The prediction is based on the previously characterized divergence data, which for purposes of clarity is referred to as a waveform. At 710, two or more waveform features of the waveform are identified.

The waveform features may be derived from specific segments of the waveform. Such segments may be selected based on certain criteria. One such criteria may be the age of the logged data. For instance, data that is too old (e.g., logged over a month ago, logged over two months ago, logged over a year ago, logged over two years ago, etc.) may be disregarded for the purpose of deriving waveform features. For further example, log data that is not contiguous for a long enough time (e.g., having time gaps in the log) may be disregarded. Other criteria may for regarding or disregarding portions of the logged data may depend on the actual values of the logged data (such as if the values logged data appear too sporadic to be trusted as representative of an operation of the VAD).

Figure 8:
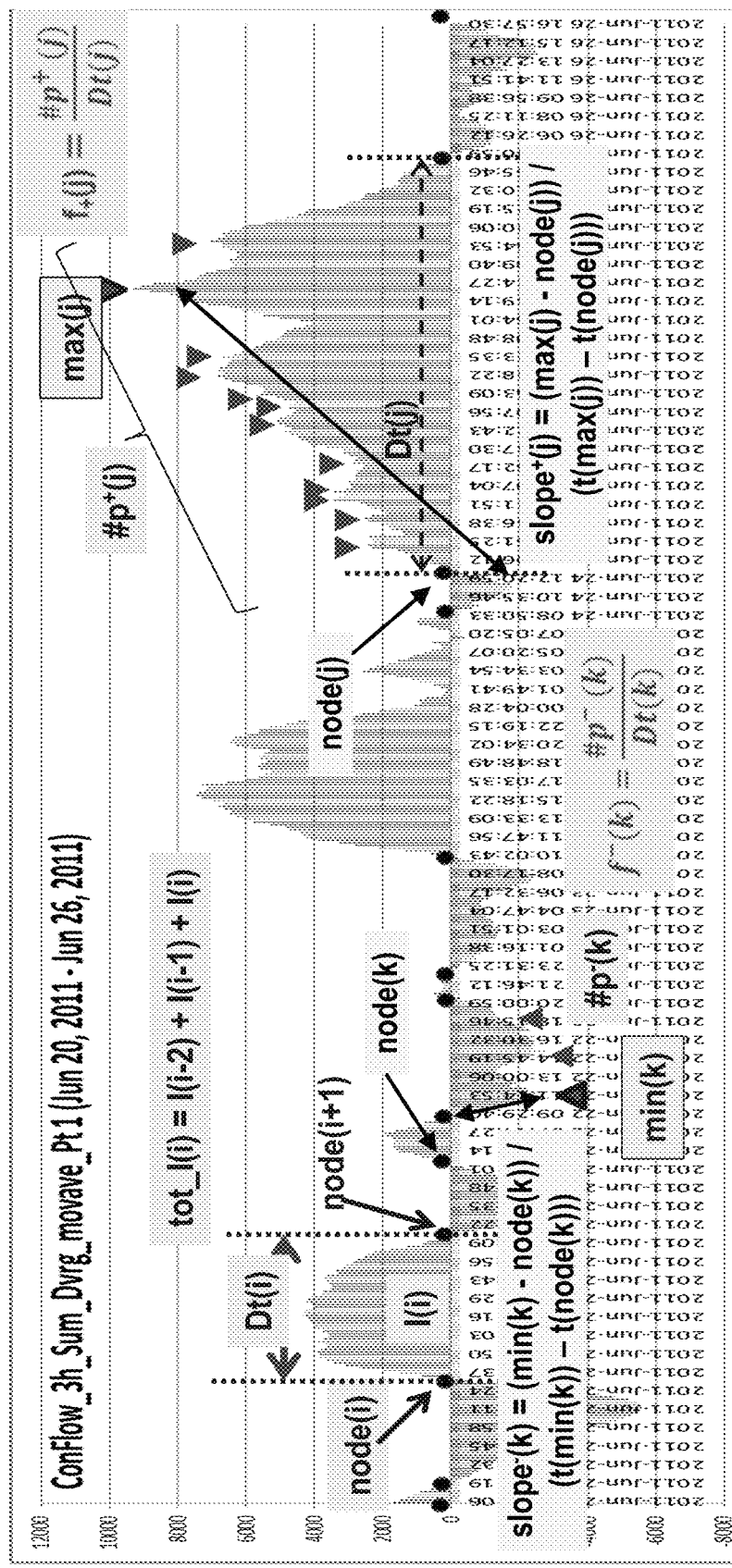
FIG. 8 is a visual representation of waveform features identified in the divergence data of FIG. 6, in accordance with an embodiment of the disclosure.

Waveform features are quantifiable features of the compiled waveform, such as maxima, minima, zero-crossing points (points for which, over the second period of time, there is a total summed divergence of about 0), local increases or decreases in the rate of divergence (slopes), etc. The following is a list of some example waveform features, as shown in FIG. 8:

node(i): A point, i, in time where the summed value equals or is approximately equal to 0 (a zero-crossing point) indicating that there was no divergence of flow during the second time span, or that there is as much positive divergence during the second time span than there is negative divergence.

Dt(i): A time segment between two consecutive nodes (i and i+1).

I(i): The integral between two consecutive nodes (i and i+1), indicating the overall sustained summed divergence for time segment Dt(i).

tot_I(i): The integral between a time point defined as zero and node i.

max(i): A maximum calculated summed divergence of flow. Max(i) may be a maximum for a predetermined span of time (e.g., one hour, one day) or for a given time segment Dt(i) or series of consecutive time segments.

min(i): A minimum calculated summed divergence of flow. Like max(i), min(i) may be a minimum for a predetermined span of time (e.g., one hour, one day) or for a given time segment Dt(i) or series of consecutive time segments.

$p^+$(i): The number of positive peaks (local maxima for a summed divergence above 0) in the divergence waveform for a given time segment Dt(i) or series of consecutive time segments.

$p^-$(i): The number of negative peaks (local minima for a summed divergence below 0) in the divergence waveform for a given time segment Dt(i) or series of consecutive time segments.

$f^+$(i): The frequency of positive peaks in the summed divergence waveform during a given time segment Dt(i) or series of consecutive time segments over which #$p^+$(i) is calculated.

$f^-$(i): The frequency of negative peaks in the summed divergence waveform during a given time segment Dt(i) or series of consecutive time segments over which #$p^-$(i) is calculated.

slope$^+$(i): The rate of summed divergence increase between a zero-crossing point and a maximum calculated divergence value (labeled in FIG. 8), or between local extrema (maxima or minima) (not labeled).

slope$^-$ (i): The rate of summed divergence decrease between a zero-crossing point and a minimum calculated divergence value (labeled in FIG. 8), or between local extrema (maxima or minima) (not labeled).

slope I(i): The rate of increase or decrease of the integral of the summed divergence (not shown).

Continuing with method 700, at 720, the waveform features derived from the summed divergence waveform of the VAD under analysis are compared to "confirmed" waveform features. The "confirmed" waveform features are waveform features derived from segments of summed divergence waveforms for which it has been confirmed whether an adverse event did or did not occur in association with those segments. Such information may include at least some data for which an adverse event is clinically confirmed (e.g., via computed tomography) to have occurred during or within some predetermined time of the confirmed data, as well as some data for which an adverse event is known not to have occurred (again, during or within a predetermined time). The predetermined time can be on the order of days (e.g., about 1 day, about 3 days, about 5 days), weeks (e.g., about 1 week, about 2 weeks, about 3 weeks), about a month, or even up to about several months.

In some examples, the waveform features may be arranged or mapped with one another, for example in n-dimensional space (n being the number of waveform features chosen to be analyzed, which may be all or a subset of the above listed features, and/or may include other features not listed). The information derived from the waveform features may be a boundary on the n-dimensional space. In this regard, a comparison between the waveform features under analysis and the confirmed waveform features may include a determination as to whether the analyzed waveform features are arranged or mapped on one or the other side of the n-dimensional space boundary.

The "confirmed" waveform features may be derived from log data collected from the VAD under analysis or from other VADs (e.g., that have been previously analyzed). In the case of using confirmed waveform features derived from the VAD presently under analysis, such confirmed waveform features may be derived from an earlier period of time for which (or prior to which) occurrence or non-occurrence of an adverse event has already been confirmed. The confirmed waveform features derived from the VAD presently under analysis may, thus, include waveform features for which it is confirmed that an adverse event did occur and/or waveform features for which it is confirmed that an adverse event did not occur.

The confirmed waveform features may be collected from the VADs (including the VAD currently under analysis) using the same or similar steps as described above. In other words, given that the waveform features of the present example are features of a flow rate divergence waveform, those features are compared to flow rate divergence waveforms of other VADs. Other factors, such as pump speed, may also be considered when determining whether confirmed waveform data is comparable to the waveform data under analysis.

The comparison of confirmed and under-analysis waveform features may involve a data mining process, in which the confirmed waveform features collectively form a set of "training" features from which to train a predictor model.

In some cases, it may be more preferable to collect training features from the VAD under analysis than from other VADs. This is because different patients carrying out different lifestyles may show different warning signs in advance of an adverse event. In the case of a first patient, a certain waveform feature (or combination of waveform features) may be indicative of an upcoming adverse event, whereas for a second patient, a different waveform feature (or different combination of waveform features) may indicate an upcoming adverse event. These features (or combination of features) effectively amount to a "signature" in the particular waveform data of a given individual. In this regard, analyzing waveform data extracted from one VAD operating in a first patient against confirmed waveform data extracted from other VADs (which had operated in other patients) may identify waveform features that generally indicate an upcoming adverse event across the larger population of VAD patients, but may not identify warning signs particular to the first patient. Thus, under such circumstances, using confirmed data from the first patient's own VAD may identify warning signs particular to the first patient that would not otherwise be recognized from a set of training data derived from VADs belonging to other patients.

In this regard, availability of operational data for the VAD under analysis over a long enough period of time may enable formulation of a patient-specific multiclass predictor model. The patient-specific model may then generate patient-centered probabilities of certain adverse events based at least in part on the patient's "signature." For example, in the case of confirmed adverse event-free operation of a VAD over a long enough course of time (e.g., about one year, two years, or more), the extended finding of adverse event-free operation may establish a strong baseline for the "normal" range of waveform features extracted from the logs of the VAD under analysis. The baseline may become even stronger (e.g., a higher level of statistical significance, enhanced performance metrics for the predictor model) as the waveform features are extracted for even longer. These over-a-year-old data may be used in addition to data from other VADs to formulate a multiclass predictor, e.g. a three-class predictive model: "normal", "abnormal-based on inherent baseline", "abnormal-based on VAD population."

Notwithstanding the possible benefits of collecting training features from the VAD under analysis, there may also be possible detriments to using such data. For example, if the patient has an adverse condition that has not been previously detected in the collected data, then such condition may bias the data, such that the collected training features may be mistakenly seen as indicative of normal operation (due to the patient's condition) rather than as indicators of an upcoming adverse event. Such bias in the training data may result in more false positives (e.g., incorrect triggering of an alarm) and/or more false negatives (e.g., failure to trigger an alarm prior to an adverse event).

Additionally, the benefits yielded by collecting training data from the VAD under analysis may gradually diminish as the collected data becomes older. For instance, a patient's "signature" may gradually change over time (e.g., with the patient's gradual lifestyle changes over time). Thus, a waveform feature (or combination of waveform features) indicating a future adverse event collected from five years earlier may be less reliable than a more recently collected feature (or combination of features).

Biasing and staleness of the training data may be mitigated by collecting data from a limited window of time. For example, the collected training features may be taken from data between one year and two years old. In such an example, since the waveform data collected from the VAD is over a full year old, it is less likely that the waveform data will be biased by a condition of the patient's (assuming, at least, that the patient has not experienced any adverse event in the previous year). Furthermore, since the waveform data is less than two years old, it is less likely that such waveform data is no longer indicative of the patient's "signature."

Additionally, in the case of extracting training features from the VAD under analysis, the extent to which features extracted from such VAD may contribute to the set of training features (e.g., for training of a predictor model) may depend on the amount of time for which that VAD has been in operation (e.g., supporting a patient). Specifically, the longer a patient is on VAD support with concomitant confirmation of a period of time with either event-free or abnormal VAD operation, the longer the waveform segments that may be available for extraction of training features for the predictor model. Thus the longer a patient is on VAD support, the heavier the contribution of features extracted from that device could be on the adverse event prediction. In contrast, during the first weeks or months of the VAD's operation, as in the prior example in which waveform data has not be logged for at least a year before the present time of analysis, prediction of adverse events may instead be based entirely or heavily on waveform features collected from the other VADs.

In the case where training features are collected from other VADs, data from one of the other VAD may be favored over data from another of the other VADs based on each VAD's similarity to the VAD under analysis. For example, the other VADs may be compared to the VAD under analysis in terms of their operating conditions, such as pump output, usual operating pump speed, and/or consumed power. In such a case, a VAD may be considered "similar" to the VAD under analysis if the VADs' operating parameters are within a percentage threshold range of each other (e.g., about 10% difference).

Thus, the other VADs may be relied on entirely or more heavily until baseline features are established for the VAD under analysis (e.g., after about one year).

At 730, the comparison of 720 is used to determine whether the identified waveform features of the VAD under analysis are more comparable to the waveform features of "abnormal" operation of a VAD for which an adverse event is known to have occurred, or are more comparable to the waveform features of "normal" or event-free operation of a VAD for which an adverse event is known not to have occurred. As explained above, this comparison may be based on data gathered from one or more VADs for which it is known whether an adverse event did or did not occur. In some examples, "abnormal" waveform features may be derived from operating data of a VAD for which occurrence of an adverse event is known, and "normal" waveform features may be derived from operating data of a VAD for which non-occurrence of an adverse event is known. In other examples, "abnormal" and "normal" waveform features may be derived from operating data of the same VAD. This may occur in the case of a VAD for which an adverse event is known to have occurred at a certain time, such that the operating data may contain time-periods with waveforms of both normal operation, which are typically chronologically distant from the time of the known adverse event, in addition to time-periods of abnormal waveform features, occurring around the time of the known adverse event.

The waveform features of the operating data collected from the other VADs may be collected in the same or a similar fashion (e.g., extracted during time-periods of various lengths, in the order of days or months) and may be stored in a database. Correlation of the waveform features to those waveform features for which an adverse event occurred may be an indication of an upcoming adverse event. Likewise, correlation of the waveform features to those waveform features for which no adverse event occurred may be an indication that no adverse event is upcoming and that the monitored VAD is operating normally.

The determination may be the result of a data mining process, such as a multivariate analysis, cluster analysis, linear discriminant analysis, Bayesian analysis, neural network analysis, k-nearest neighbor algorithm, decision tree, or any combination of the above. Depending on the number of waveform features that are selected, as well as the particular waveform features that are selected, the above analyses may be utilized to classify the various time periods of VAD operation (e.g., subsets of the full waveforms) of the other VADs. Such classifications may be used to train a statistical model, which in turn may be used to provide a corresponding probability of occurrence of an adverse event.

In some cases, the determination of an oncoming adverse event may further include a determination as to the type of oncoming adverse event. For example, if it is known that a particular waveform feature (or combination of waveform features) is indicative of a certain type of adverse event, that the identification of such waveform feature(s) may be used to determine that such type of adverse event is likely to occur. As a further example, if it is known that the confirmed waveform features that are most similar to the waveform features under analysis (e.g., on the same side on the n-dimensional boundary) were derived from segments of logged data that occurred prior to a certain type of adverse event, then the similarity to those waveform features may be indicative of an oncoming occurrence of the same type of adverse event. In other words, confirmed log data may be classified into different types of adverse events, and the data under analysis may be compared to the different classes of confirmed data to identify a particular type of adverse event.

In some scenarios, analysis may involve classifying the chosen waveform features into two separate non-overlapping classes (e.g., features corresponding to occurrence of an adverse event, and features corresponding to non-occurrence of an adverse event). However, in other scenarios, the analysis of the selected waveform features may not result in entirely separating the compared waveform features into two classes. Also, sometimes the identified waveform features may not neatly fall into one of the two classes. Therefore, in any of the above scenarios, the determination of an oncoming adverse event may further involve attributing a percentage likelihood of an upcoming adverse event. Any of the above statistical analyses may be utilized to derive the percentage likelihood.

In other cases, the waveform features may be classified into more than two classes. For example, the features may be further characterized by certain types of adverse events, thus resulting in more than two classifications (e.g., more than two boundaries in the n-dimensional space). The number of classes that the predictor utilizes may depend on the discrete types of confirmed data and corresponding types of adverse events or absence thereof (e.g., clinical characterizations attributed to the operational data gathered from various patients on VAD support).

Prediction of an adverse event may be further based on other information about the patient using the monitored VAD. Such information may include patient history information (e.g., a patient's activity level, medication, and/or hematocrit levels, various pathologies of known conditions of the patient, and/or previously documented adverse events). Patient history information may vary over time; therefore, the patient history information itself may be discretized in one or more waveforms representing the evolution of individual, time-dependent variables. Patient history information may alternatively be used in a form of various weighted combinations (or features) in the aforementioned statistical analyses (e.g., data mining processes) and in addition to the features extracted from the waveforms of the VAD signals.

The method of FIG. 7 may be performed repeatedly, as often as is necessary in order to predict adverse events. For instance, the characterized divergence data may be subjected to the above predictive analysis on a daily or weekly basis, or any other basis in between. For example, the VAD control circuit may be operable to transmit summed divergence data logged for a previous amount of time (e.g., between about 6 days and 60 days) to a remote system. Upon receipt of the logged data, the remote system may run the above predictive analysis. Any determinations (e.g., presence or absence of oncoming adverse event, etc.) may then be transmitted back to the VAD in order to notify the patient and/or may be transmitted to a clinician to notify the clinician and for further analysis.

In addition to prediction of cerebrovascular accidents (ischemic or hemorrhagic stroke or transient ischemic attacks), the methods and systems of the present disclosure are also capable of identifying onset of thrombosis in a patient using a VAD, since thrombosis may affect VAD operational parameters (e.g. flow rate through the VAD or consumed power). In this respect, the present disclosure by generating a prediction window in the order of days or weeks, may provide an integral tool in a clinical decision system by enabling the timely clinical intervention and prevention of the aforementioned adverse events.

If an adverse event or other undesirable health condition is predicted or identified during analysis of the VAD operating data (including, in some cases, a type of undesirable condition), an alert or notification may be triggered (e.g., by the control circuit) to notify the patient and/or clinician of the prediction/identification. The notification may further provide a reasoning or explanation as to how the decision to provide an alert was made (e.g., identifying any one or combination of a particular time, particular waveform feature, particular operating parameter of the VAD, etc., associated with the determination, etc.). The notification may further indicate whether the determination of an upcoming adverse event is based on a comparison to operating data of the VAD under analysis, a comparison to operating data of other VADs, or a combination thereof. Such information may contribute to further clinical decision making and analysis for preventive treatment for VAD patients at a high risk of an adverse event. The notification may also include a calculated probability of an onset of the predicted adverse event, the probability being based on the analysis, as described above.

Linear discriminant analyses in accordance with the above methods were tested using data collected from 14 patients, 9 of whom were known to have experienced cardiovascular accidents within days to weeks after the collection of the analyzed data, and the other 5 of whom were known to have not experienced an adverse cardiac event. In total, 2,671 sample nodes (e.g., output of 410 in FIG. 4) were analyzed. These analyses were conducted using various combinations of the waveform features described in FIG. 8. In other words, in some tests all of the waveform features were used to classify the nodes, and in other tests only some of the waveform features were used while the remaining waveform features were disregarded.

In one test analysis, the following waveform features were used: Dt(i); I(i); tot_I(i); max(i); min(i); #p$^+$(i), and slope$^+$(i). The overall results of the analysis correctly predicted an oncoming CVA for most of the 9 affected patients, and corrected indicated no CVA for the remaining 5 patients. More specifically, of the 2,671 nodes tests, only 170 nodes from the patients who experienced a CVA were incorrectly classified as "no CVA" (false negative). and only 4 nodes from the normal patients were incorrectly classified as "CVA" (false positive). This translates to an overall sensitivity of about 78% (about 7-8 out of every 10 patients at risk correctly diagnosed), an overall specificity of about 99% (only 1 of out every 100 healthy patients sent to the emergency room due to false alarm), and a balanced accuracy (average of sensitivity and specificity) of about 86%. Moreover, given that the analysis performed with relatively high sensitivity, with only a minimal drop off in specificity, the analysis resulted in an area-under-the-curve of about 99%.

As an alternative or supplement to the example method of FIG. 7, calculating the likelihood of an adverse cardiac event may be based on sorting the characterized divergence data (e.g., the summed divergence values) by magnitude. In such an example, an adverse cardiac event may be predicted using only the highest magnitude values of the sorted values. For instance, if operating data from a VAD produces several sustained data points of divergence data significantly exceeding previous divergence values, this may be indicative of an onset of an adverse cardiac event.

The above examples describe prediction of an adverse event using flow rate data from a VAD. In other examples, prediction of an adverse event may be additionally or alternatively based on other operating parameters, such as power supply or pressure differential across the pump. Moreover, VAD operating parameters may be supplemented with information about the patient using the monitored VAD. Such information may include patient history information (e.g., a patient's activity level, medication, and/or hematocrit levels).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of characterizing divergence of a monitored flow rate of blood through an implantable blood pump, comprising a control circuit repeatedly performing over time:
   determining a flow rate of blood through the pump at a then-current time,
   calculating an average flow rate of blood through the pump over a first period of time preceding the then-current time,
   repeatedly calculating a plurality of divergence values, which is representative of a difference between the average flow rate and the determined then-current flow rate, wherein the divergence of flow rate is characterized based on a sum of the calculated plurality of divergence values,
   compiling the summed plurality of divergence values into a waveform,
   predicting the adverse event based on a plurality of features of the waveform, and
   generating a notification representative of a predicted adverse event based on the sum of the plurality of divergence values, the adverse event being one of a group consisting of a cerebrovascular accident and a thrombus.

2. A method as recited in claim 1, wherein for a given then-current time, the summed plurality of divergence values are the divergence values calculated over a second period of time immediately preceding the then-current time.

3. A method as recited in claim 2, wherein the second period of time is shorter than the first period of time.

4. A method as recited in claim 2, wherein the second period of time is about three hours, and wherein the first period of time is about three days.

5. A method as recited in claim 1, wherein the calculated average flow rate is a moving average, and wherein the first period of time immediately precedes the then-current time.

6. A method of predicting an adverse event based on flow rate data from an implantable blood pump, the method comprising the method of characterizing divergence of a monitored flow rate recited in claim 1, wherein each of the summed plurality of divergence values is associated with its corresponding then-current time.

7. A method as recited in claim 6, wherein the waveform is a time-domain waveform.

8. A method of predicting an adverse event based on flow rate data from an implantable blood pump, the method comprising the method of characterizing divergence of a monitored flow rate recited in claim 1, wherein each of the summed plurality of divergence values is associated with its corresponding then-current time, and further comprising sorting the summed plurality of divergence values by magnitude, and predicting the adverse event based on the highest magnitude summed plurality of divergence values.

* * * * *